United States Patent [19]

Emmons et al.

[11] 3,939,200

[45] Feb. 17, 1976

[54] ALIPHATIC ACYL-CONTAINING AMINE HYDROCHLORIDES

[75] Inventors: William D. Emmons, Huntingdon Valley; Jerome F. Levy, Dresher, both of Pa.

[73] Assignee: Rohm and Haas Company, Philadelphia, Pa.

[22] Filed: Sept. 4, 1970

[21] Appl. No.: 69,965

Related U.S. Application Data

[63] Continuation-in-part of Ser. No. 518,977, Jan. 6, 1966, Pat. No. 3,567,763.

[52] U.S. Cl......... 260/482 R; 260/404.5; 260/468 J; 260/470; 260/471 R; 260/478; 260/481 R; 260/482 P
[51] Int. Cl.[2]....................................... C07C 101/26
[58] Field of Search .................... 260/482 R, 468 J

[56] References Cited
UNITED STATES PATENTS
2,871,258   1/1959   Hidalgo et al. ..................... 260/482

*Primary Examiner*—Lorraine A. Weinberger
*Assistant Examiner*—Paul J. Killos

[57] ABSTRACT

Novel acyl-containing amine hydrochlorides are produced by first converting the amino group or groups of an amino acid to an acid salt by reaction with hydrochloric acid and the resulting product is reacted with an alkanolamine or diol in an inert liquid medium while passing a stream of hydrogen chloride gas therethrough. The amine hydrochlorides produced in this manner may be converted to the corresponding isocyanates by reaction with phosgene or other carbonyl dihalide.

8 Claims, No Drawings

ALIPHATIC ACYL-CONTAINING AMINE HYDROCHLORIDES

CROSS-REFERENCE TO RELATED APPLICATION

This application is a continuation-in-part of copending U.S. Serial No. 518,977, filed on January 6, 1966 now U.S. Pat. No. 3,567,763.

This invention relates to a novel group of acylcontaining amines and to the salts of these amines with strong acids.

It has long been known that aliphatic isocyanates impart premium properties to urethanes derived therefrom in terms of light stability and similar properties. However, conventional aliphatic isocyanates such as hexamethylene diisocyanate are characterized by extreme toxicity which renders their handling and use extremely hazardous. Accordingly, they have been produced only in limited amounts at a corresponding high unit cost. Aliphatic isocyanates derived from the phosgenation of the amine hydrochlorides produced from ester amines are also known. However, the ester amines themselves have heretofore been produced by the reaction of an alkanolamine hydrochloride with either an acid chloride or acid anhydride. The necessity of using the acid chloride or acid anhydride in the production of the ester amine has rendered these intermediates expensive to produce and thus has limited, if not prevented, the commercial use of the isocyanates produced therefrom.

We have now discovered an entirely new class of aliphatic, alicyclic, and aromatic amines and their salts and the isocyanates corresponding thereto which may be produced from readily available raw materials in good yield under simple process conditions. The novel amines and amine salts are useful not only as intermediates in producing the described novel isocyanates, but are further useful in themselves for curing epoxy resins, as intermediates in the production of other compounds and for condensation with formaldehyde and formaldehyde-containing materials such as urea-formaldehyde resins.

The novel amines of the invention can be represented by the following Formulas I, II, and III:

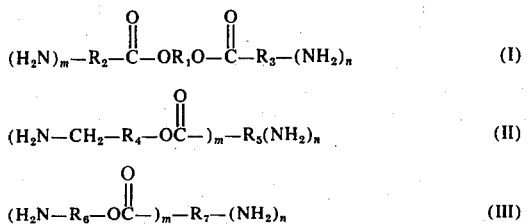

wherein m and n are either one or two, $R_1$ is the diester residue of an alkane or cycloalkane diol having two primary hydroxyl groups, preferably from 2 to 18 carbon atoms, and up to one hetero oxygen or sulfur atom, $R_2$ and $R_3$ are divalent alkylene or cycloalkylene radicals having, preferably 3 to 18 carbon atoms, $R_4$ is an alkylene or cycloalkylene radical having, preferably 1 to 7 carbon atoms and up to one hetero oxygen or sulfur atom, $R_5$ is a divalent organic arylene or aralkylene radical having, preferably 6 to 12 carbon atoms, $R_6$ is an alkylene or cycloalkylene radical having, preferably 2 to 8 carbon atoms and up to one hetero oxygen of sulfur atom, and $R_7$ is a divalent organic alkylene or cycloalkylene radical having, preferably 3 to 18 carbon atoms.

The aliphatic amines of formulas I and III are preferred. A particularly useful class of amines includes those amines of formula III in which $R_7$ is n-pentylene.

The amine salts of the invention can be represented by the following Formulas IV, V, and VI:

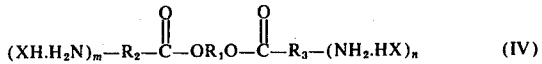

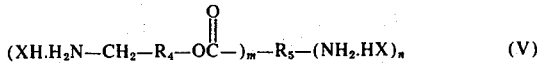

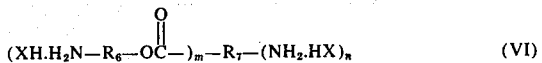

wherein $m$, $n$, $R_1$, $R_2$, $R_3$, $R_4$, $R_5$, $R_6$, $R_7$, are as defined above and HX is a strong mineral acid, such as hydrochloric acid, hydrobromic acid, hydrofluoric acid, hydroiodic acid, sulfuric acid, phosphoric acid, and the like. The hydrochloride salts are preferred.

In the instant invention, the amino groups of the novel amines and amine salts are provided in whole or in part by an amino acid. The amino acids which are useful in the invention are the monoamino-monocarboxylic acids, the monoaminodicarboxylic acids, the diamino-monocarboxylic acids, and diamino-dicarboxylic acids, preferably having 3 to 18 carbon atoms, and lactams, preferably having 3 to 12 carbon atoms in the ring. The novel amines and their salts in which the amino groups are provided in part by an amino acid are produced by reacting one or more of the designated class of amino acids as its acid salt with an alkanolamine salt, such as the hydrochloride. The novel amines and their salts wherein the amino groups are provided wholly by an amino acid are produced by reacting a monoamino-monocarboxylic acid or a lactam with a dihydroxy alcohol (hereinafter referred to as "diols"), the amino groups being converted to an acid salt before the esterification reaction. In addition, novel compounds containing four amine groups are produced by reacting a diamino-monocarboxylic acid with a diol. Preferably, these esterification reactions are carried out while passing a stream of hydrogen chloride gas through the reaction mixture while the esterification proceeds.

To produce the acyl-containing amines of the invention and their salts, the amino group or groups of the amino acid are first converted to an acid salt by reaction with a strong acid, preferably hydrochloric acid, and the resulting product is then reacted with an alkanolamine (also converted to a strong acid salt, such as the hydrochloride) or a diol in an inert liquid reaction medium. The amino acid and the diol or alkanolamine must have a significant solubility in each other under the reaction conditions or else the inert liquid used as the reaction medium must be a mutual solvent for these materials. The reaction temperature may be from about 40°C. to the temperature at which the amine acid salts present in the reaction mixture dissociate into the free amine. Preferably the reaction is carried out at from about 50°C to 180°C. Desirably an esterification catalyst is used to promote the reaction. Suitable catalysts include, for example, p-toluenesulfonic acid, hydrochloric acid, chlorosulfonic acid, etc. In a preferred embodiment of the invention, a stream of hydrogen chloride gas is passed through the reaction mixture while the reaction proceeds, in which case no separate catalyst for the esterification is needed. Means should be provided to distill off or otherwise remove the water formed during the esterification. The reaction may be carried out at sub-atmospheric or superatmospheric pressures but preferably is carried out at atmospheric pressure. Liquid reaction media which may be used for the esterification include aromatic hydrocarbons, chlorinated aromatic hydrocarbons, chlorinated aliphatic hydrocarbons, chlorinated alicyclic hydrocarbons, tetramethylenesulfone, etc. Where one of the reactants is a liquid or is molten under the reaction conditions, an excess of such reactant may be used as the reaction medium so long as such excess does not cause polymerization or promote other undesirable side-reactions, i.e., such excess must act as an inert liquid. In certain instances where the reaction product itself is a liquid under the reaction conditions, it apparently acts as the inert liquid, the initial esterification forming the first quantities of such product occurring in the presence of water (which is later distilled off as esterification proceeds) which is a solvent for the amine salts.

When a lactam is used as the amino acid, desirably water (preferably about one mole per mole of lactam) is added along with a strong acid (preferably hydrochloric acid) to facilitate opening the ring. An undue excess of water is to be avoided since it must be removed during the esterification and such removal is a significant item of cost. The lactam may be first heated in contact with the water-acid mixture to open the ring, and then the alcohol, diol or alkanolamine added along with an inert organic liquid and an azeotropic agent and the ester prepared as described above preferably using a stream of hydrogen chloride gas. Alternatively, all the reagents may be charged initially, the mixture heated without removal of water for a sufficient time to open the ring, and then the water removed causing esterification to proceed. In this latter case, it is sometimes desirable to conduct the ring opening in a sealed pressure vessel under autogenous pressure. Other variations may also be used, as initially charging all the materials except the azeotropic agent which is added after ring opening. The use of water in this manner is not essential and good results have been obtained without its use.

The amine salts which are produced according to the process of the invention can be converted to the free amines by any of the processes known in the art, such as neutralization of the strong acid, heating to the salt dissociation temperature, extraction, and the like.

The amines and amine salts which are produced in this manner may be converted to the corresponding isocyanates by reaction with phosgene or other carbonyl dihalide. Phosgene may be employed in either liquid or gaseous form. The amine or amine salt is dispersed in an inert liquid reaction medium, phosgene added, preferably in excess of that needed to react quantitatively with the amino groups present, and the temperature of the reaction medium maintained at from about 100°C. to 225°C. The molar ratio of phosgene to amine hydrochloride group may be from about 1.1:1 to 10:1 and preferably is at least 2:1. Suitable liquid reaction media include aromatic hydrocarbons, chlorinated aromatic hydrocarbons, chlorinated aliphatic hydrocarbons, chlorinated alicyclic hydrocarbons, etc. The phosgenation can also be carried out in steps. A purified amine or amine salt can be used for the phosgenation or, if desired, the crude reaction product of the reaction between the amino acid and the alkanolamine salt or diol may be used.

The alkanolamines which may be used in the instant invention preferably contain from 2 to 8 carbon atoms, have one primary or secondary hydroxyl group and one primary amino group and may include one hetero oxygen or sulfur atom in the alkyl chain. The alkyl gruop of the alkanolamine may be substituted with inert substituent groups as alkyl, alkoxy, nitro, halogen, and the like. Particularly preferred alkanolamines are ethanolamine, 2-(2-aminoethoxy)-ethanol, 1-amino-2-propanol, 2-amino-1-propanol, 2-methyl-2-amino-1-propanol, 3-amino-1-propanol and 2-amino-1-butanol. Mixtures of alkanolamines may be used.

The diols which may be used are those having two primary hydroxyl groups, preferably from 2–18 carbon atoms, including aromatic and aliphatic diols. The alkylene and cycloalkylene diols may have a hetero oxygen or sulfur atom and may be substituted with inert substituent groups as alkyl, nitro, halogen, etc. Among the diols which can be used are the $\alpha,\omega$-aliphatic diols, p-bis(hydroxymethyl) cyclohexane, p-phenylenedimethylene diol, diethylene glycol, etc. Mixtures of diols may be used.

The amino acids which may be used in the instant invention may be either optically active or inactive and includes monoamino-monocarboxylic acids such as alanine, glycine, isoleucine, 3-aminobutyric acid, 3-aminopropionic acid, 3-amino-2-methyl propionic acid, 3-amino-3-methylbutyric acid, 12-aminolauric acid, phenyl alanine, p-aminobenzoic acid, methionine, $\omega$-amino acids generally, etc.; monoamino-dicarboxylic acids such as aspartic acid and glutamic acid; diamino-monocarboxylic acids such as lysine and ornithine; diamino-dicarboxylic acids such as lanthionine; and lactams such as $\beta$-methyl-$\beta$-butyrolactam, $\alpha,\beta$-dimethylbutyrolactam, $\alpha,\alpha,\beta$-trimethylbutyrolactam, $\beta$-carbomethoxybutyrolactam, $\beta$-phenyl-$\beta$-propiolactam, $\beta$-methyl-$\beta$caprolactam, $\beta$-methyl-$\beta$-valerolactam, 2-piperidone, 2-pyrrolidone, 6-methyl-2-piperidone, $\epsilon$-caprolactam, 3-methyl-$\epsilon$-caprolactam and 7-methyl-$\epsilon$-caprolactam, and the like. The amino acids may be substituted with inert substituent groups as alkyl, nitro, halogens, etc. and may contain one or more hetero atoms which do not interfere with the esterification reaction, and, where applicable, the subsequent phosgenation. Mixtures of amino acids may be used. The diaminomonocarboxylic acids disclosed in French Pat. No. 1,351,368 may be used. Amino acids occur widely in nature and a number of synthesis methods are available for their production from inexpensive raw materials. Thus the addition of ammonia to an unsaturated acid may be used to produce inexpensive amino acids for use in the instant invention.

The isocyanates produced by the phosgenation of the acyl-containing amines and amine salts have several unusual properties. With respect to the aliphatic isocyanates, these isocyanates possess the advantages of the aliphatic isocyanates of the prior art in respect to light stability. However, they differ significantly from the aliphatic isocyanates of the prior art such as hexamethylene diisocyanate in possessing substantially reduced toxicity.

The novel isocyanates prepared from the amines and amine salts of the invention may be used as crosslinking agents for polymers containing active hydrogen groups, may be reacted with low molecular weight polymers containing active hydrogen groups such as hydroxyl-terminated polyesters or polyethers to produce polyurethanes, and may be added to polymeric compositions to improve the adhesion thereof to a variety of substrates, particularly metallic substrates. They are also useful as intermediates in producing other novel compounds useful as insecticides, herbicides, etc.

The following examples will further illustrate this invention but are not intended to limit it in any way.

EXAMPLE 1

A four-necked, round-bottomed flask fitted with a mechanical stirrer, a thermometer, a gas inlet tube, and a Dean-Stark water separator trap was charged with 91.5 g. (1.50 moles) of ethanolamine, 540 ml. of o-dichlorobenzene and 240 ml. of benzene. Hydrogen chloride was passed in through the gas inlet tube to convert all of the ethanolamine to its hydrochloride salt, following which 188.3 g. (1.50 mole) of 3-aminopropionic acid hydrochloride was added. With hydrogen chloride being passed in at the rate of 150 ml./min., the reaction mixture was heated to reflux (112°–120°) and kept at that temperature until the theoretical amount of water had azeotroped over and no more water was being evolved. This required a total of approximately 20 hours. The solvent was then decanted and the solid product was dried in a vacuum oven to give 292.0 g. (95% of theoretical) of β-aminoethyl 3-aminopropionate dihydrochloride, m.p. 186°–192°C. Recrystallization from ethanol raised the melting point to 196-198°C.

Anal. calc'd for $C_5H_{14}Cl_2N_2O_2$: C, 29.28%; H, 6.88%; Cl, 34.58%; N, 13.66%. Found: C, 29.28%; H, 6.82%; Cl, 34.61%; N, 13.64%.

EXAMPLE 2

Using the process described in Example 1, β-aminoethyl 2-aminoacetate dihydrochloride was produced. After recrystallization from ethanol, the product had a melting point of 166°–168°C.

EXAMPLE 3

Using the process described in Example 1, β-aminoethyl 6-aminocaproate dihydrochloride was produced from ethanolamine and 6-aminocaproic acid. After recrystallization from isopropanol, the product had a melting point of 198°–199°C.

EXAMPLE 4

The apparatus of Example 1 was charged with 61 g. (1.00 mole) of ethanolamine and 500 ml. of tetramethylene sulfone. Hydrogen chloride (1.0 mole) was passed in, following which 173.5 g. (1.00 mole) of p-aminobenzoic acid hydrochloride was added. With hydrogen chloride being passed in at the rate of 1.5 moles/hr., the temperature was raised to 150°C. and sufficient benzene was added to obtain good refluxing at that temperature. After a total of 10 hours of refluxing, 24.5 ml. of 10 N hydrochloric acid had been collected in the azeotrope trap. The reaction mixture was cooled, diluted with 750 ml. of benzene and filtered. The solid was triturated with a warm mixture of approximately equal parts of acetone and isopropanol, cooled and filtered; yield of crude β-aminoethyl p-aminobenzoate dihydrochloride 141 g., m.p. 225°–230°C. Recrystallization from isopropanol raised the m.p. to 235°C.

Anal. calc'd for $C_9H_{14}Cl_2N_2O_2$: N, 11.07%. Found: N, 10.85%.

EXAMPLE 5

The apparatus of Example 1 was charged with 15.0 g. (0.15 mole) of 4,4-dimethyl azetidinone-2, 14.7 g. (0.15 mole) of ethanolamine hydrochloride and 50 ml. of 1,2,3-tichloropropane. The mixture was cooled to 0°C. and 0.25 mole of hydrogen chloride was passed in. Cooling was stopped, and after about 10 minutes an exotherm carried the temperature to 50°C. The mixture was heated to 110°C. to insure completion of the reaction. The solvent was decanted and the crude β-aminoethyl 3-amino-3-methylbutyrate dihydrochloride, a viscous oil, was digested with 100 ml. of isopropanol, cooled and filtered to give 22.8 g. of material melting 203°–205°C; and after recrystallization from ethanol, m.p. 206°–206.5°C.

Anal. calc'd for $C_7H_{18}Cl_2N_2O_4$: C, 36.06%; H, 7.78%; Cl, 30.41%; N, 12.02%. Found: C, 35.88%; H, 7.75%; Cl, 30.27%; N, 11.83%.

EXAMPLE 6

The apparatus of Example 1 was charged with 30.6 g. (0.500 mole) of ethanolamine and 360 ml. of o-cresol. Hydrogen chloride (1 mole) was passed in following which 56.6 g. (0.500 mole) of ε-caprolactam was added. The reaction mixture was heated at 150° for a total of 14 hours while still passing in hydrogen chloride. Then most of the solvent was distilled off under reduced pressure, heating with a steam bath. The residue was treated with approx. 0.5 l. of acetone and the crude β-aminoethyl 6-aminocaproate dihydrochloride, 65 g., was removed by filtration. Recrystallization from isopropanol gave pure material melting 185°–189°C., mixed m.p. with authentic material undepressed.

EXAMPLE 7

The apparatus of Example 1 was charged with 19.7 g. (0.10 mole) of 2-azacyclotridecanone, 6.2 g. (0.10 mole) of ethanolamine and 100 ml. of o-cresol. Hydrogen chloride (0.20 mole) was passed in while the mixture was held at 80°C. then, adjusting the hydrogen chloride flow to 0.5 mole/hr., the temperature was raised to 140°–150°C. and maintained there for 25 hours. The reaction mixture was then cooled to cause precipitation of the crude β-aminoethyl 12-aminolaurate dihydrochloride, 7.5 g. Recrystallization from isopropanol gave an analytical sample, m.p. 240°C.

Anal. calc'd for $C_{14}H_{32}Cl_2N_2O_2$: Cl, 21.40%; N, 8.46%. Found: Cl, 20.97%; N, 8.46%.

EXAMPLE 8

The apparatus of Example 1 was charged with 51.3 g. (0.25 mole) of β-aminoethyl 3-aminopropionate dihydrochloride and 360 ml. of chlorobenzene. The reaction mixture was heated at reflux while gaseous phosgene was passed in through the gas inlet tube at the rate of 90 ml./min. for a total of 6.3 hours. Then 270 ml. of o-dichlorobenzene was added and the reaction mixture was phosgenated at reflux (137-142°C) for an additional 6.8 hours. Unreacted β-aminoethyl 3-aminopropionate dihydrochloride, 23 g., m.p. 190°–196° was removed by filtration. Solvent was distilled from the filtrate under reduced pressure and the product was distilled, b.p. 110°–115°C. under 1.0 mm. Hg. pressure, weight 13.0 g., corresponding to 51% of the theoretical yield of β-isocyanatoethyl 3isocyanatopropionate when corrected for the recovered starting material.

Anal. calc'd for $C_7H_8N_2O_4$: C, 45.65%; H, 4.38%; Cl, 0.00%; N, 15.21%. Found: C, 45.49%; H, 4.25%; Cl, 0.00%; N, 15.42%.

EXAMPLE 9

The apparatus of Example 1 was charged with 1.00 mole of β-aminoethyl 6-aminocaproate dihydrochloride and 575 ml. of o-dichlorobenzene. The mixture was phosgenated for 5.3 hours at 130°–147°C. using a phosgene flow of approximately 0.75 mole/hr. The solvent was distilled off under reduced pressure and the product was distilled through a molecular still at 160° at 1–2 mm. pressure to give a 77% yield of β-isocyanatoethyl 6-isocyanatocaproate. Analysis for isocyanate functionality indicated a purity of 94%. An analytical sample was prepared by ordinary distillation, b.p. 128°C. (0.25 mm.).

Anal. calc'd for $C_{10}H_{14}N_2O_4$: C, 53.09%; H, 6.24%; N, 12.38%; eq. wt. 113.1 g/eq. Found: C, 53.11%: H, 6.17%; N, 12.50%; eq. wt. 113.5 g/eq.

EXAMPLE 10

Using the process described in Example 9, the crude β-aminoethyl p-aminobenzoate dihydrochloride produced in Example 4 was phosgenated at 150°C. for 15 hours and at 180°C. for 4 hours. The product boiled at 140°–150°C. (0.4 mm. Hg). Analysis showed that the product contained 86% β-isocyanatoethyl p-isocyanatobenzoate and 12% tetramethylene sulfone.

EXAMPLE 11

The apparatus of Example 1 was charged with 59 g. (0.50 mole) of 1,6-hexanediol, 75.1 g. (1.00 mole) of glycine and 250 ml. of 1,2,3-trichloropropane. The reaction mixture was heated to 145°C. and sufficient benzene was added to maintain a good reflux rate at that temperature, then kept at 145°C. for a total of 3.5 hours while hydrogen chloride was being passed in/at the rate of 1.3 moles/hr. At the end of the heating period, a total of 21.4 ml. of ca. 10 N hydrochloric acid had collected in the azeotrope trap. On cooling the reaction mixture, the 1,6-di-(2-aminoacetoxy)-hexane dihydrochloride separated as a thick oil which on digestion with 450 ml. of isopropanol crystallized to give 81 g. of crude product, melting 167°–200°C, after beginning to soften at 152°C.

Anal. calc'd for $C_{10}H_{22}Cl_2N_2O_4$: Cl, 23.23%. Found: Cl, 22.73%.

EXAMPLE 12

The apparatus of Example 1 was charged with 15.5 g. (0.25 mole) of ethylene glycol, 83.7 g. (0.50 mole) of 6-aminocaproic acid hydrochloride and 150 ml. of toluene. The mixture was heated at reflux for 7 hours with hydrogen chloride being passed in at the rate of ca. 80 ml. per minute. At the end of this period the aqueous phase in the trap amounted to 11.4 g. and, as approximately 10 N hydrochloric acid, contained 0.43 mole of water. The crude 1,2-di(6-aminocaproyloxy)ethane dihydrochloride was removed by filtration and recrystallized first from a mixture of isopropanol and toluene and then from a mixture of isopropanol and hexane to give a crude product, m.p. ca. 100°C., in 80% yield. Several more crystallizations gave an analytical sample.

Anal. calc'd for $C_{14}H_{30}Cl_2N_2O_4$: Cl, 19.63%; N, 7.75%. Found: Cl (ionizable), 19.5%; N, 8.02%.

EXAMPLE 13

The apparatus of Example 1 was charged with 56.6 g. (0.50 mole) of ε-caprolactam and 400 ml. of 1,2,3-trichloropropane. Hydrogen chloride (0.9 mole) was passed in, then 22.5 g. (0.25 mole) of 1,4-butanediol was added and the mixture was heated for about 5 hours at 145°–148°C., adding a little benzene to get a good reflux rate. A total of 6 ml. of water had azeotroped over. The reaction mixture was cooled, diluted with 400 ml. of acetone and filtered. The solid was heated with an additional 200 ml. of acetone, cooled and filtered to give 18.8 g. of crude 1,4-di-(6-aminocaproyloxy)-butane dihydrochloride, m.p. 180°–185°C. An analytical sample was prepared by recrystallization from a mixture of isopropanol and acetone, m.p. 192°–197°C.

Anal. calc'd for $C_{16}H_{34}Cl_2N_2O_4$: C, 49.35%; H, 8.80%; Cl, 18.21%; N, 7.20%. Found: C, 49.26%; H, 8.99%; Cl, 18.24%; N, 7.27%.

EXAMPLE 14

The apparatus of Example 1 was charged with 8.9 g. (0.070 mole) of 1,6-hexanediol, 14.9 g. (0.150 mole) of 4,4-dimethyl azetidinone-2 and 50 ml. of 1,2,3-trichloropropane. This was cooled to −5°C. and over a period of one hour, hydrogen chloride (0.25 mole) was passed in, keeping the temperature between −10° and +5°C. Then, with the hydrogen chloride flow still at 0.25 mole/hr., the mixture was heated to 135°C. which took 1/3 hour. The reaction was complete at this point. The 1,6-di-(3-amino-3-methylbutyryloxy)hexane dihydrochloride was removed by filtration, washed well with benzene and dried in a vacuum oven at 75°C. overnight; yield 27.2 g. (100% of the theoretical amount), m.p. 210°–213°C.

Anal. calc'd for $C_{16}H_{34}Cl_2N_2O_4$: Cl, 18.21%. Found: Cl(ionizable) 18.21%.

Recrystallization from a mixture of isopropanol and ethanol raised the melting point to 219-220°C.

Anal. calc'd for $C_{16}H_{34}Cl_2N_2O_4$: C, 49.35%; H, 8.80%; Cl, 18.21%; N, 7.20%. Found: C, 49.47%; H, 8.80%; Cl, 18.22%; N, 7.23%.

EXAMPLE 15

Using the method described in Example 12, 1,4-di(6-aminocaproyloxy)-butane dihydrochloride was produced by reacting 1,4-butanediol with 6-aminocaproic acid hydrochloride. The reaction took about 2.5 hours at 110-120°C.

EXAMPLE 16

The apparatus of Example 1 was charged with 81.0 g. (0.268 mole) of 1,6-di-(2-aminoacetoxy)-hexane dihydrochloride, m.p. 162°–167°C., and 240 ml. of o-dichlorobenzene. This mixture was phosgenated for 2 hours at 125°–133°C. using a phosgene flow rate of 0.75 mole/hr. The solvent was distilled under reduced pressure to leave the crude 1,6-di-(2-isocyanatoacetoxy)-hexane as a dark oil. The crude 1,6-di-(2-isocyanatoacetoxy)-hexane is reacted with aniline to form 1,6-bis-[2-(N-phenylureido)-acetoxy]-hexane, m.p. 131°–140°C.

Anal. Calc'd for $C_{24}H_{30}N_4O_6$: (the aniline derivative): N, 11.91%. Found: 11.23%.

EXAMPLE 17

Using the method of Example 16, 45 g. of di(6-aminocaproyloxy)-hexane dihydrochloride was phosgenated in 1,2,3-trichloropropane to yield 29.1 g. of crude 1,6-di-(6-isocyanatocaproyloxy)-hexane.

EXAMPLE 18

The apparatus of Example 1 (with a condenser in place of the separator trap) was charged with 56.5 g. (1.0 mole) of ε-caprolactam and 42 ml. of 37% aqueous hydrochloric acid (1.0 mole). This was heated under reflux for two hours to hydrolyze the lactam, then cooled to 50°–60°C. 3-Aminopropanol (37.5 g., 0.5 mole) was added slowly, following which 0.5 mole of hydrogen chloride was passed in, keeping the temperature below 85°C. Then 200 ml. of o-dichlorobenzene and 100 ml. of benzene were added. The condenser was replaced by a Dean-Stark trap and the mixture was heated under reflux at 115°C. while a slow stream of hydrogen chloride was passed in. Benzene had to be added from time to time to maintain a good reflux rate at 115°C. When no more water was being collected in the azeotrope trap and the esterification was thus complete, the benzene was distilled off under reduced pressure and replaced with another 100 ml. of o-dichlorobenzene.

This mixture was then phosgenated for 4 hours at 150°C. using a phosgene flow rate of 1.5 moles/hr. After cooling, the liquid portion of the reaction mixture was decanted from some solid which formed in the flask and was then stripped of solvent and distilled on a wiping film still (100°–150°C. at 1 mm. pressure). Analysis for isocyanate content by reaction with butylamine indicated a purity of 95%. A derivative was obtained by reaction of the isocyanate with two equivalents of aniline, m.p. 138°–144°C.

Anal. calc'd for $C_{23}H_{30}N_4O_4$: C, 64.77%; H, 7.09%; N, 13.14%; O, 15.00%. Found: C, 64.04%; H, 7.09%; N, 12.71%; O, 15.19%.

EXAMPLE 19

The apparatus of Example 18 was charged with 113.2 g. (1.0 mole) of ε-caprolactam and 1.0 mole of concentrated aqueous hydrochloric acid. This solution was refluxed for one hour with hydrogen chloride gas being passed in at the rate of 0.5 mole/hr. Then 89.0 g. (1.0 mole) of 2-aminobutanol dissolved in 100 ml. of benzene and 300 ml. of o-dichlorobenzene was added over a half-hour period, raising the flow of gaseous hydrogen chloride to 1 mole/hr. during this addition. The mixture was then heated under reflux while a slow stream of hydrogen chloride was passed in. The reflux temperature was kept at 115°C. by periodically adding benzene to the mixture as needed. After a total of 16.5 hours of reflux, no more water was being collected and the esterification was complete.

The mixture was phosgenated at 140°C. for 4 hours then at 150°C. for 2 more hours, using a phosgene flow of 2 moles/hr. Benzene, which distilled into the Dean-Stark trap, had to be drawn off in order to heat to the desired temperature. The reaction mixture was decanted from a small amount of a tarry material and stripped of solvent. The product was distilled on a wiping film still at 250°C. (0.5 mm), then redistilled conventionally, b.p. 138°C. (0.15 mm). Analysis for isocyanate content by reaction with butylamine indicated a purity of 99%.

The diisocyanate was tested for differential reactivity by adding one mole of 2-ethoxyethanol (1 equivalent) to 1 mole of the diisocyanate dissolved in o-xylene (2 equivalents), heating the mixture to 75°C. and following the reaction using vapor phase chromatography. If both isocyanate groups have the same reactivity, the product will contain 25% of the molecules wherein neither isocyanato group has reacted (there would also be 25% with both groups reacted and 50% with only one group reacted). With 92±2% of the alcohol reacted, the product contained only 11±2% of the diisocyanate indicating a high degree of differential reactivity.

EXAMPLE 20

The apparatus of Example 18 (set for total reflux) was charged with 113 g. (1.0 mole) of ε-caprolactam and 89 g. (1.0 mole) of 2-amino-2-methylpropanol followed by the gradual addition of 2.2 moles of concentrated hydrochloric acid. After refluxing for 3 hours, most of the water was stripped off under reduced pressure, keeping the temperature of the reaction mixture below 85°C. during the stripping. Then the still-head was replaced by a Dean-Stark trap, 450 ml. of o-dichlorobenzene was added and the mixture was heated to 115°C. while a slow stream of hydrogen chloride was passed into the mixture. Enough benzene was added at this point, and as required later to maintain a good rate of reflux at 115°C. Refluxing was continued in this way until no more water was being collected, then the benzene was distilled off under reduced pressure and replaced by 100 ml. of o-dichlorobenzene.

The mixture was phosgenated for 4 hours at 130°C, then for 2 hours at 140°C, using a phosgene flow of approximately 2–2.5 moles/hr. After cooling and decanting the solution, the solvent was distilled off under reduced pressure and the isocyanate was distilled on a wiping film still to give a sample of the isocyanate contaminated with a chlorine containing by-product. The analytical sample was obtained by preparative vapor phase chromatography.

Anal. calc'd for $C_{12}H_{18}N_2O_4$: C, 56.68%; H, 7.14%; N, 13.14%; O, 25.17%. Found: C, 57.24%; H, 7.24%; N, 12.71%; O, 24.49%.

A derivative prepared by reacting the diisocyanate with two equivalents of cyclohexylamine melted 135°–150°C after several recrystallizations from isopropanol-water.

Anal. calc'd for $C_{24}H_{44}N_4O_4$: C, 63.68%; H, 9.80%; N, 12.38%; O, 14.14%. Found: C, 63.73%; H, 10.16%; N, 12.20%; O, 14.30%.

The diisocyanate was tested for differentail reactivity using dry ethanol with dibutyltin-dilaurate catalyst. A strong exotherm occurred upon addition of the ethanol-catalyst solution and subsided in about 15 minutes indicating substantially complete reaction of the primary isocyanate group. About 2.3 hours later, approximately 49% of the isocyanate groups had reacted. The half-life of the remaining isocyanate groups was found to be about 8 hours.

By comparison, the isocyanate groups in β-isocyanatoethyl-6-isocyanatocaproate were found to have about equal reactivity.

EXAMPLE 21

A four-necked, round-bottomed flask fitted with a mechanical stirrer, a distillation head, a thermometer and a dropping funnel was charged with 147 g. (1.00 mole) of L—(+) glutamic acid and 336 g. (5.51 moles) of ethanolamine. Then 730 g. (ca. 7.2 moles) of 36–38% aqueous hydrochloric acid was added slowly, cooling the reaction mixture to keep the temperature below 60°C. Most of the water was distilled off under reduced pressure not heating above 90°C. at 30 mm. Hg pressure. Following the stripping, the distillation head and the dropping funnel were replaced by a Dean-Stark trap and a gas inlet tube. Toluene (100 ml.) was added and the mixture was heated under reflux (115°C) for 30 hours while hydrogen chloride was being passed in at the rate of 0.4 mole/hr. The ethanolamine hydrochloride being molten at the reaction temperature, the excess of this material together with the toluene acts as the solvent. At the end of this period, no more water was being azeotroped over, the molten reaction mixture was poured into 1000 ml. of ethanol, cooled to room temperature and filtered. This crude product was recrystallized once from a smaller volume of ethanol to give 127 g. of di-β-aminoethyl glutamate dihydrochloride, m.p. 168°–172° C.

One hundred twenty-three grams of the above salt was suspended in 700 ml. of o-dichlorobenzene and, with phosgene being passed in at the rate of 0.75 mole/hr., the mixture was heated at 135°C. for 6 hours, then the temperature was raised to 178° gradually over another 6-hour period. The reaction mixture was cooled, filtered and the solvent was distilled off under reduced pressure. The product was distilled on a wiping film still using a wall temperature of 250°C. (0.4 mm. Hg.), yield 70.3 g.

Anal. calc'd for $C_{12}H_{13}N_3O_7$: C, 46.31%; H, 4.21%; N, 13.50%. Found: C, 46.41%; H, 4.37%; N, 13.67%.

EXAMPLE 22

Using the method of Example 13, 1,6-di-(6-aminocaproyloxy)-hexane dihydrochloride was produced from ε-caprolactam and 1,6-hexanediol. After recrystallization from a mixture of isopropanol and acetone, the product had a melting point of 180°–185°C.

Among the other amines which are conveniently prepared by the processes of the above examples are 3-aminopropyl 6-aminocaproate, 5-aminopentyl 6-aminocaproate, 3-chloro-4-aminobutyl 5-aminopentanoate, 12-aminododecyl 8-aminooctanoate, 3-aminocyclopentyl 4-aminobutyrate, 3-ethyl-5-aminopentyl 6-aminocaproate, 4-aminocyclohexyl 3-aminopropionate, 4-aminohexyl 6-aminocaproate, and the like.

In both the specification and claims, reference is made to passing the hydrogen chloride gas "through the reaction mixture". As is obvious to those skilled in the art, this result may be achieved either by bubbling a stream of hydrogen chloride through the reaction mixture or by initially treating the reaction mixture with hydrogen chloride and then maintaining a flow of hydrogen chloride gas over the surface of the reaction mixture so that the gas passes from the atmosphere within the reaction vessel into the reaction mass itself. By this means, removal of hydrogen chloride by the azeotroping of the water is compensated for and the reaction medium is kept relatively saturated with hydrogen chloride throughout the esterification reaction.

It is to be understood that changes and variations may be made without departing from the spirit and scope of the invention as defined by the appended claims.

We claim:

1. An amine having the formula

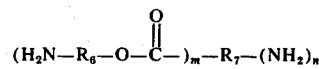

wherein $m$ and $n$ are either 1 or 2,
$R_6$ is an alkylene or cycloalkylene radical having 2 to 8 carbon atoms and up to one hetero oxygen or sulfur atom in the alkylene chain, and
$R_7$ is a divalent organic alkylene or cycloalkylene radical having 3 to 18 carbon atoms.

2. An amine according to claim 1 wherein $m$ and $n$ are both 1.

3. An amine according to claim 1 wherein $m$ is 2 and $n$ is 1.

4. An amine according to claim 2 wherein $R_7$ is a n-pentylene radical.

5. An amine according to claim 4 wherein $R_6$ is an ethylene radical.

6. An amine salt having the formula

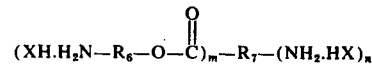

wherein $m$ and $n$ are either 1 or 2,
$R_6$ is an alkylene or cycloalkylene radical having 2 to 8 carbon atoms and up to 1 hetero oxygen or sulfur atom in the alkylene chain,
$R_7$ is a divalent organic alkylene or cycloalkylene radical having 3 to 18 carbon atoms, and
HX is a strong mineral acid.

7. An amine salt according to claim 6 wherein $m$ and $n$ are both one, and $R_7$ is a n-pentylene radical.

8. An amine salt according to claim 7 wherein $R_6$ is an ethylene radical and HX is hydrochloric acid.

* * * * *